United States Patent [19]

Schaefer

[11] Patent Number: 5,014,969

[45] Date of Patent: May 14, 1991

[54] PATIENT SUPPORTING TABLE HAVING A SUPPORT PLATE PROVIDED WITH A CUT-OUT AND HAVING A BASE MEMBER CARRYING THE SUPPORT PLATE

[75] Inventor: Willi Schaefer, Erlangen, Fed. Rep. of Germany

[73] Assignee: Siemens Aktiengesellschaft, Munich, Fed. Rep. of Germany

[21] Appl. No.: 539,898

[22] Filed: Jun. 18, 1990

[30] Foreign Application Priority Data

Jun. 30, 1989 [EP] European Pat. Off. ......... 89111995.0

[51] Int. Cl.$^5$ ............................................. A61G 13/00
[52] U.S. Cl. .................................................... 269/322
[58] Field of Search .............................. 269/322–328; 5/431, 448; 378/209; 108/20, 143, 137, 102

[56] References Cited

U.S. PATENT DOCUMENTS

| | | | |
|---|---|---|---|
| 2,897,029 | 7/1959 | Maisel | 269/323 |
| 3,428,307 | 2/1969 | Hunter et al. | 378/209 |
| 3,747,916 | 7/1973 | Benson | 269/322 |
| 3,751,028 | 8/1973 | Scheininger et al. | 378/209 |
| 4,545,571 | 10/1985 | Chambron | 269/322 |
| 4,568,071 | 2/1986 | Rice . | |
| 4,575,064 | 3/1986 | Menor | 269/322 |
| 4,674,505 | 6/1987 | Pauli et al. . | |
| 4,823,774 | 4/1989 | Grasser | 269/322 |
| 4,869,483 | 9/1989 | Wiesmet | 269/322 |

FOREIGN PATENT DOCUMENTS

| | | |
|---|---|---|
| 0255645A1 | 2/1988 | European Pat. Off. . |
| 0294679A1 | 12/1988 | European Pat. Off. . |
| 2759079 | 7/1979 | Fed. Rep. of Germany . |
| 2013178 | 7/1969 | France . |

OTHER PUBLICATIONS

Siemens Aktiengesellschaft Bereich Medizinische Technik—Erlangen brochure entitled "Lithostar Universeller urologischer Arbeitsplatz fur Therapie und Diagnostik", pp. 2–7.

Dorner Lithotripter MPL 9000; *Contours of a Revolution*.

*Primary Examiner*—Robert C. Watson
*Attorney, Agent, or Firm*—Hill, Van Santen, Steadman & Simpson

[57] ABSTRACT

A patient supporting table having a base member and a support plate adjustably carried on the base member. The support plate is provided with a cut-out through which the surface of a patient lying on the support plate is accessible for medical purposes. The base member comprises an opening the extent (b) of which is less than the extent (a) of the cut-out, so that the base member additionally supports a portion of a patient lying on the support plate in the region of the cut-out, particularly when the support plate is positioned relative to the base member such that the cut-out of the support plate leaves the opening of the base member free.

10 Claims, 6 Drawing Sheets

PATIENT SUPPORTING TABLE HAVING A SUPPORT PLATE PROVIDED WITH A CUT-OUT AND HAVING A BASE MEMBER CARRYING THE SUPPORT PLATE

BACKGROUND OF THE INVENTION

The invention is directed to patient supporting tables having a support plate with a seating surface for a patient and a cut-out through which the body surface of a patient lying on the seating surface is accessible for medical purposes. The invention is also directed to patient supporting tables comprising a base member that carries the support plate such that the support plate is adjustable relative to the base member.

Patient supporting tables of the type described above are required for a great variety of applications wherein it is necessary that the body surface of a patient be accessible through the cut-out, whether to permit an operative procedure to be performed or to permit application of a medical device, for example, a lithotriptor, to the body surface of the patient. The support plate is adjustable relative to the base member in order to be able to position the patient as desired.

Such a patient supporting table is disclosed and described in a brochure published by Siemens AG, and entitled: "LITHOSTAR Universeller urologischer Arbeitsplatz fuer Therapie und Diagnostik". The printing reference number is A91001-M1027-G490-01 PA 4864.

In the disclosed patient supporting table, a shockwave source is arranged under the support plate and the table is provided with a rectangular cut-out. The shockwave source is provided for outputting focused shockwaves for disintegrating calculi, for example kidney stones, situated in the body of the patient.

For such a treatment, a shockwave tube is brought into engagement with the body surface of a patient lying on the support plate through the cut-out of the support plate. The tube then is acoustically coupled to the body surface of the patient so that the calculus to be disintegrated is situated in the focus of the shockwaves. Under the influence of a series of focused shockwaves generated by the shockwave tube, the calculus disintegrates into fragments that can be eliminated in a natural way.

In order to be able to bring the calculus to be disintegrated into the focus of the shockwaves, an exact positioning of the patient relative to the shockwave tube is required. Thus, the disclosed patient supporting table provides means including a drive motor for displacing the support plate together with the patient lying thereon relative to the base member and the shockwave tube along the longitudinal direction of the table and/or transversely relative thereto.

In order to prevent the patient (who may be sedated or even anesthetized under certain circumstances) from falling through the cut-out, the cut-out has only relatively small dimensions in the longitudinal direction of the table. Moreover, since the shockwave tube is arranged in the cut-out of the support plate during the displacement of the support plate, the support plate can be displaced only by a slight dimension in the longitudinal direction of the table relative to the shockwave tube. Otherwise, edges of the cut-out would strike against the shockwave tube and displace it out of its predetermined position, or worse, damage it.

Therefore, attending physicians and attending personnel must first manually align the patient at least in the longitudinal direction of the table with sufficient precision on the support plate so that the range of adjustment of the support plate limited by the dimensions of the shockwave tube and of the cut-out is adequate for an exact positioning of the patent. In view of the fact that the patient can be sedated or anesthetized, this involves considerable physical exertion on the member of the attending physicians and the attending personnel. Moreover, there is also the risk that a patient who, for example, is already is exactly positioned in the transverse direction of the patient supporting table will be in turn dislocated out of that position. Further, the described procedure is not particularly gentle on the patient since considerable forces can be exerted on the patient.

SUMMARY OF THE INVENTION

The invention provides a patient supporting table wherein an exact positioning of a patient located thereon relative to a cut-out in the table is possible in a simple way without involving physical exertion on an attending physician or personnel, without the exertion of significant forces on the patient, and without risk that the patient will fall through the cut-out.

To these ends, the invention provides in an embodiment, a patient supporting table with a support plate adjustably supported on a base member, wherein:
a) the base member is arranged under the support plate and has an upper side that faces toward an underside of the support plate;
b) the support plate includes a patient access cut-out;
c) the base member includes an opening extending through the upper side thereof whose extent in the adjustment direction is less than a corresponding extent of the cut-out of the support plate;
d) the support plate is positionable relative to the base member such that the opening of the base member is positioned within the cut-out of the support plate; and
e) the upper side of the base member forms an additional seating surface within the cut-out of the support plate.

In order to enable access to the body surface of a patient lying on the support plate, the support plate is positioned relative to the base member such that edges of the cut-out of the support plate do not extend over the opening of the base member. As a consequence of the fact that the base member comprises a plate-shaped surface that forms a weight bearing surface in the region of the cut-out of the support plate and as a consequence of the fact that the opening of the base member comprises an extent in adjustment direction that is less than that of the cut-out of the support plate, a patient lying on the support plate is additionally supported by the plate-shaped upper side of the base member in the region of the cut-out. This structure is expedient for the purpose of an effective support of the patient when the surface of the base member is only a slight distance from the seating surface, i.e., the thickness of the patient support plate is relatively slight.

The dimensions of the opening of the base member are selected such that a region of the body surface of a patient lying on the support plate which corresponds to the respective medical purpose is accessible. The dimensions of the cut-out, by contrast, are dimensioned at least in the adjustment direction such that without exercising special care, it is possible to position a patient on the support plate so that region of the patient's body surface that must be accessible for the respective medical purpose is situated within the cut-out. By adjusting the support plate relative to the base member, the relevant region of the body surface of the patient is then brought over the opening of the base member. It is thus adequate to roughly pre-position the patient on the support plate in order to then be able to exactly position the patient by adjusting the support plate relative to the base member, doing this without particular physical exertion on the member of the attending physicians and the attending personnel. The positioning event is also gentle on the patient since only slight forces need be exerted on the patient.

It is impossible for the patient to slide through the cut-out or, respectively, through the opening.

In one embodiment, the invention provides additional support of the patient in the region of the cut-out by allowing the support plate to have at least the edges of the cut-out be positioned essentially gap-free against the upper side of the base member. This construction simultaneously reduces the risk that skin folds of the patient can be pinched between the support plate and the base member when adjusting the support plate. This risk of pinching can be reduced further by providing the seating surface of the support plate with a cushion that extends up to the edges of the cut-out, since having the body surface of the patient lie against the upper side of the base member directly in the region of the edges of the cut-out is avoided by this construction.

In order, for the sake of a good additional support of the patient by the upper side of the base member, to avoid an excessively great distance between the seating surface of the support plate and the surface of the base member, it is advantageously provided in another embodiment of the invention, that the support plate is constructed as a thin-walled component member.

In an especially advantageous embodiment of the invention, it is provided that the underside of the support plate facing away from the seating surface is fashioned as a surface of action that presses against a correspondingly shaped surface of action of the base member; that the surfaces of action extend to the edges of the cut-out, or respectively, of the opening that extends transversely relative to the adjustment direction; and that the surfaces of action of the support plate and of the base member slide on one another when the support plate is adjusted relative to the base member. Particularly when the support plate is constructed as a thin-walled component member, the support plate is assured to have adequate support provided by the base member. Further, it is guaranteed, without additional outlay, that the upper side of the base member is only a small distance away from the seating surface of the support plate and thus provides additional support of the patient in the region of the cut-out because the support plate lies against the upper side of the base member essentially gap-free in the region of the cut-out.

It is provided in another embodiment of the invention that the cut-out is a recess in one of the edges of the support plate and the opening is a recess in a corresponding edge of the base member. As a result, the body surface of the patient is easily accessible not only directly from below but also laterally from below.

The construction of the opening of the base member as a recess can be realized in a technologically simple way when the base member comprises two plate members that, relative to the adjustment direction, are positioned at different sides of the opening, and when the plate members are joined to one another with a carrying beam that extends along that edge of the support plate lying opposite the recess, extending therealong at least in the region of the recess of the support plate. The carrying beam thereby serves not only to join the two plate members of the base member but also effects an effective support and reinforcement of the support plate.

It is provided in an embodiment of the invention that the support plate can be optionally attached to the base member such that the recess is situated at the one or at the other side of the patient supporting table. Since patient supporting tables usually comprise a defined foot end and a defined head end, this construction guarantees that the improved patient accessibility provided by the recess cut-out can be utilized for both body sides of the patient. The same advantage is also provided when the support plate comprises two plate sections, whereby one plate section includes the recess and can be optionally connected to the other plate section such that the recess can be positioned at the one or at the other side of the patient supporting table. The additional advantage provided by this construction is that, not the entire support plate, but only the plate section provided with the recess be turned for changing the position of the recess, this being capable of being accomplished in a significantly easier way.

In a further embodiment of the invention, when the support plate can be turned such that the recess can be situated at the one or at the other side of the patient supporting table, two carrying beams are provided that, depending on the position of the recess at the one or at the other side of the patient supporting table, can be optionally extended, so that a reliable support of the support plate is guaranteed regardless of the position of the recess at the one or at the other side of the patient supporting table and, at the same time, the recess of the base member is oriented corresponding to the recess of the support plate.

These and other features will become apparent with reference to the following detailed description of the presently preferred embodiments and accompanying drawings.

DETAILED DESCRIPTION OF THE PRESENTLY PREFERRED EMBODIMENTS

Figure 1:
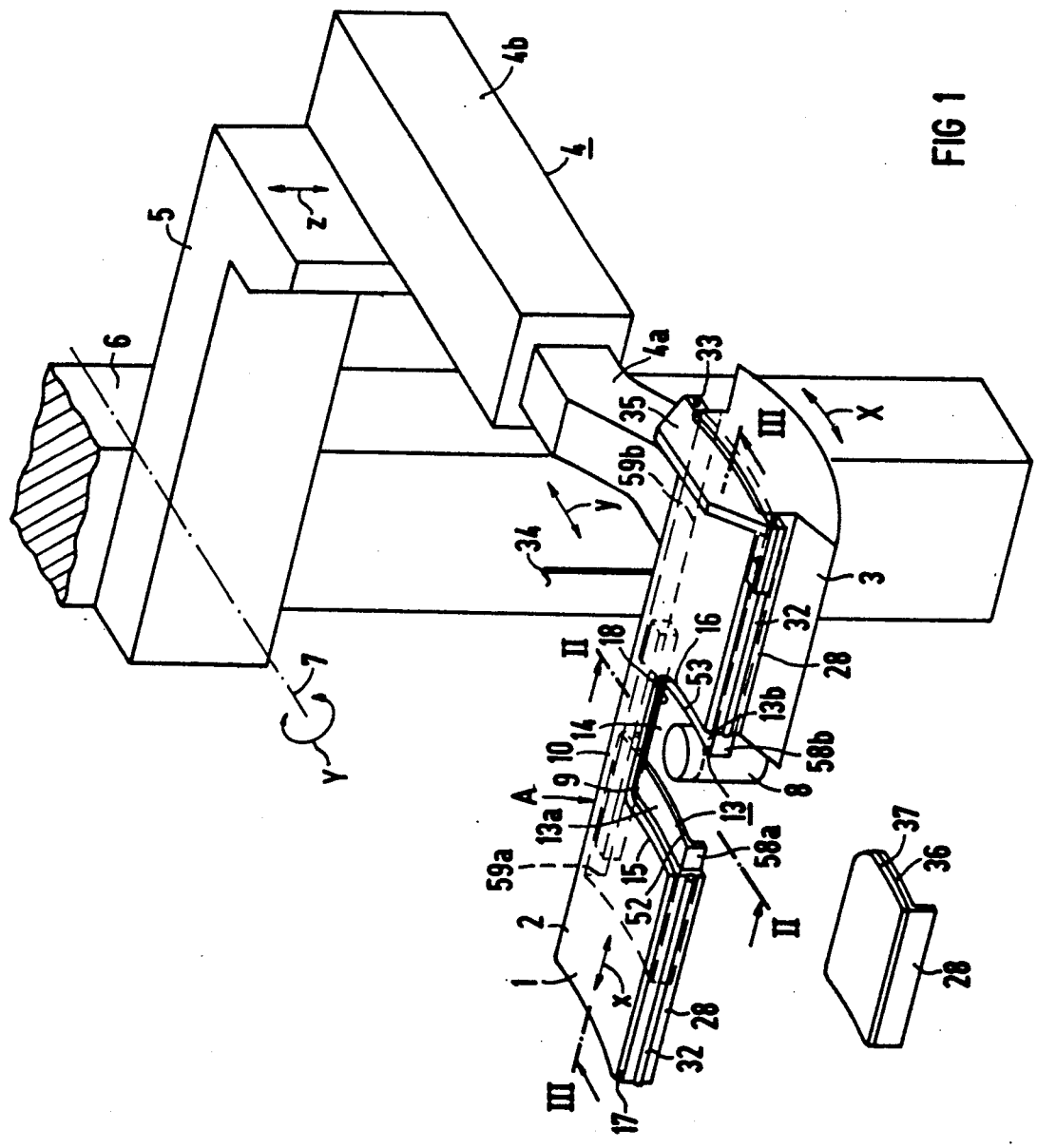
FIG. 1 a respective view of a patient supporting table.

FIGS. 1 through 5 illustrate a patient supporting table that is a component member of a work station for treating a patient with focused shockwaves, for example for non-invasive disintegration of calculi such as kidney or gall stones situated in the body of the patient. The focused shockwaves are generated by means of a shockwave source as disclosed, for example, in German Published Application 33 28 051, and are introduced into the body of a patient to be treated.

To that end, the shockwave source has its application end formed by a flexible bellows brought into engagement with the body surface of the patient such that an acoustic coupling is provided. The patient and the shockwave source are thereby positioned relative to one another by an appropriate adjustment of the patient supporting table and of the shockwave source such that the calculus to be disintegrated is situated in the focus of the shockwaves. The calculus disintegrates into fine fragments under the action of a plurality of shockwaves, these fragments being capable of being eliminated by the patient in a natural way.

The illustrated patient supporting table has a support plate 1 with a seating surface 2 for the patient. A base member 3 that carries the support plate 1 is also provided, whereby the support plate 1 can be separated from the base member 3.

The patient supporting table has its base member 3 attached to a carrying member 4 with suitable articulation means (not shown) such that it is pivotable about an axis that extends parallel to its longitudinal axis, as indicated by the curved double arrow X. A carrying member 4 comprises two arm members 4a and 4b inserted into one another in telescoping fashion, so that the patient supporting table is adjustable in the direction of the double arrow y, i.e., transversely relative to the direction of the longitudinal axis, and in a plane that is parallel to the seating surface 2. The arm member 4b of the carrying member 4 is secured to an arm-shaped carrier 5 via suitable guide means (not shown) such that the patient supporting table is adjustable at a right angle relative to the plane of its support plate 1, as indicated by the double arrow z. The arm member 4a slides in and out of the arm member 4b.

The carrier 5 is secured to a stand 6 by suitable articulation means (not shown), so as to be pivotable about an axis 7 that extends transversely relative to the longitudinal axis of the patient supporting table and parallel to the plane of the support plate 1. The carrier 5 is pivotable in the direction of the double arrow y. The support plate 1 is adjustable along a straight line in the direction of the longitudinal axis of the patient supporting table relative to the base member 3, as indicated by the double arrow x.

In order to be able to execute the above-described adjustment motions, electric motors and suitable gearings (neither shown) are provided, these being actuatable by an attending person with a suitable control unit (also not shown). Only a drive means provided for the adjustment of the support plate 1 relative to the base member 3 in the direction of the longitudinal axis of the patient supporting table (double arrow x) is schematically illustrated in FIG. 3.

As illustrated, the drive means comprises an electric motor 54, arranged in the base member 3, that drives a threaded spindle 55. The threaded spindle 55 interacts with a nut 56 that is detachably secured to the support plate 1 in a way that is not illustrated. A slot 60 through which the nut 56 is in engagement with the support plate 1 is provided in the base member 3.

Figure 3:
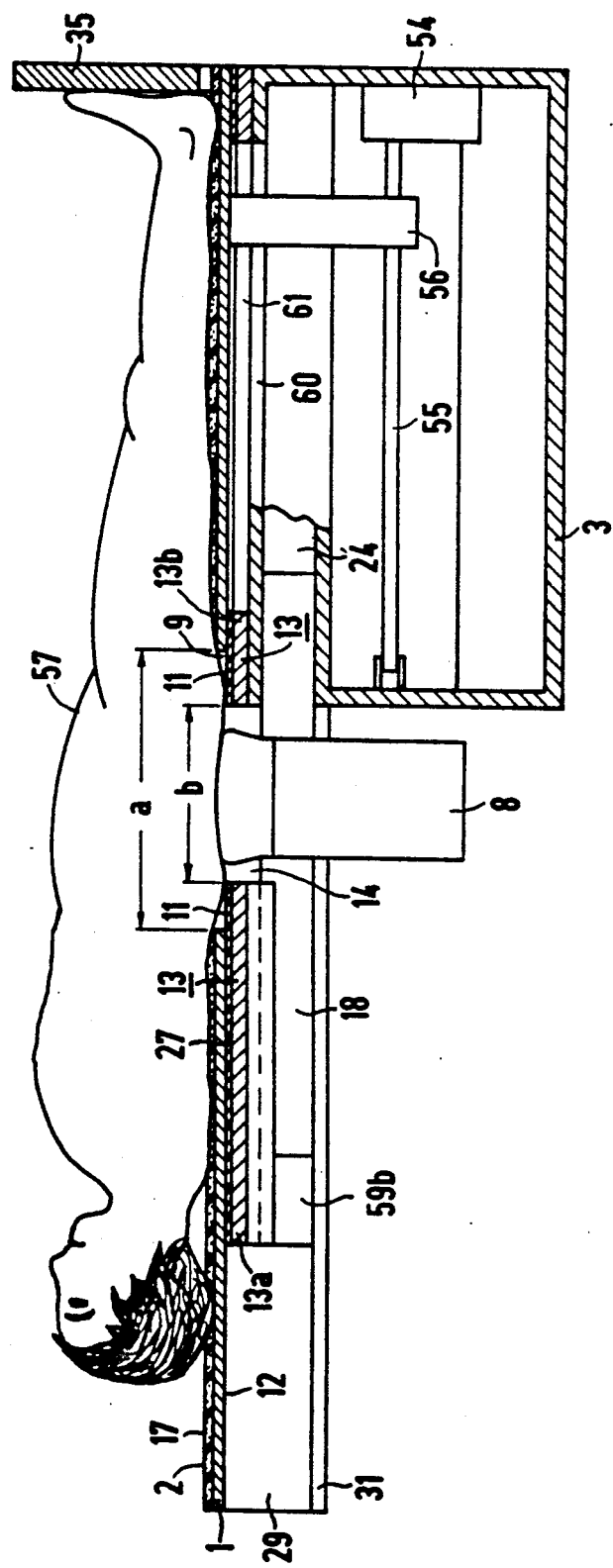
FIG. 3 is a cross-sectional view of the patient supporting table of FIG. 1 generally taken along the longitudinal line III—III in FIG. 1.
Figure 5:
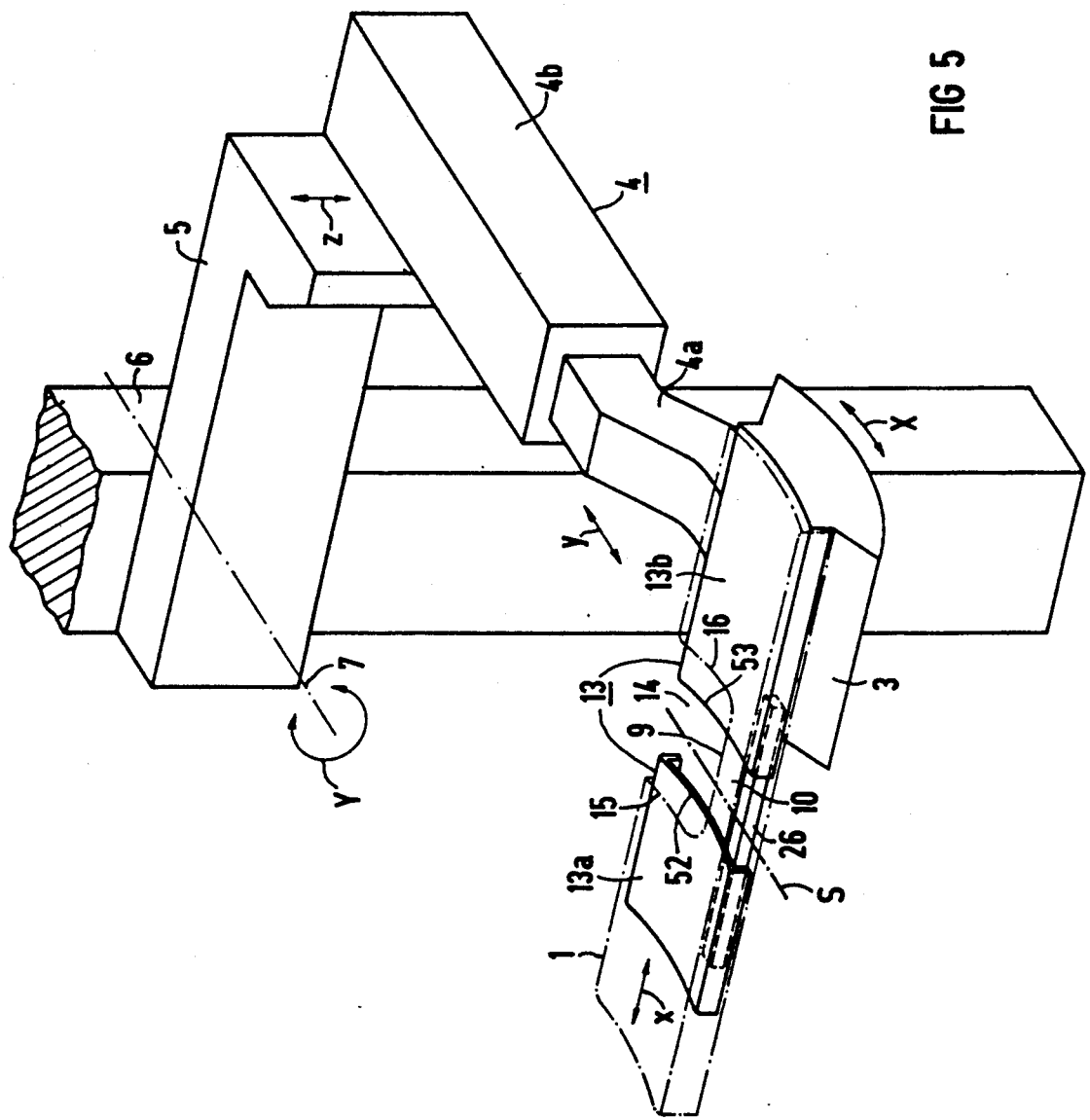
FIG. 5 perspective view of the patient supporting table of FIG. 1 when the support plate is turned.

It becomes clear from FIGS. 1, 3, and 5 that the patient supporting table has its base member 3 attached to the carrying member 4 such that the patient supporting table is supported only at its one end. The supported end of the patient supporting table is the foot end thereof. The free end of the patient supporting table forms the head end thereof. As a consequence of the fact that the patient supporting table is supported at only its one end, accessibility to the patient supporting table or, respectively, to a patient lying thereon is improved.

Figure 2:
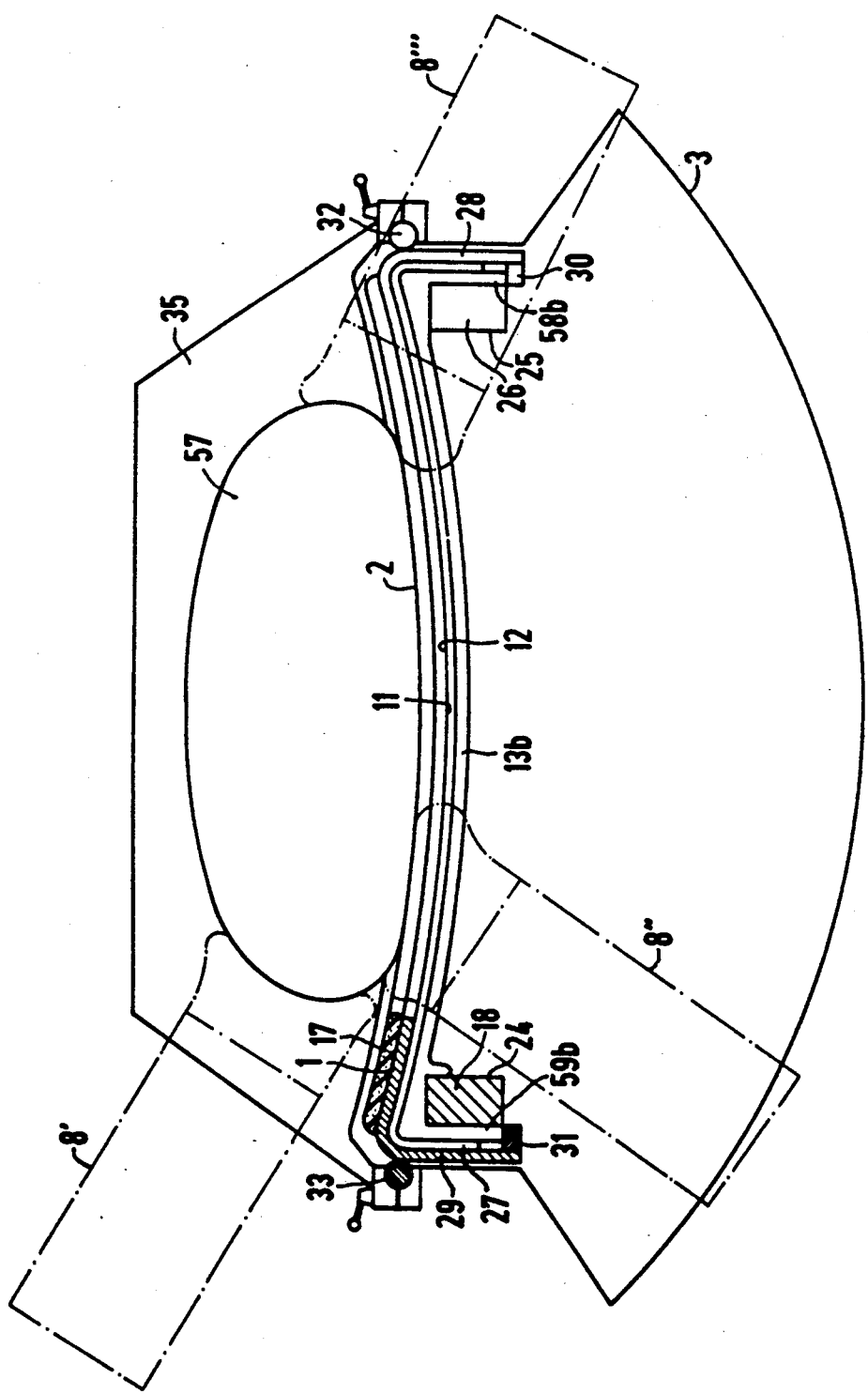
FIG. 2 is a cross-sectional view of the patient the line II—II in FIG. 1.

A shockwave source 8 is schematically illustrated in FIG. 1. The shockwave source 8 is attached to a suitable mount (not shown). In order to be able to apply the shockwave source 8 to the body surface of a patient lying on the support plate 1 from optimally arbitrary directions, the support plate 1 is provided with a cut-out that is executed as an approximately rectangular recess 9 in what is the front longitudinal edge of the support plate 1 (see FIG. 1). As can be seen in FIG. 2 with reference to the extreme positions of the shockwave source 8 illustrated by broken lines 8' and 8'', only a relatively small angular range of the shockwave source 8 is blocked by a section 10 of the support plate 1 remaining in the region of the recess 9. In particular, it is possible to laterally couple the shockwave source 8 to the body 57 of the patient from below at an oblique angle. This position of the shockwave source 8 is illustrated by broken lines 8'''.

In order to enable positioning of the patient relative to the shockwave source 8 by displacing the support plate 1 in the direction of the longitudinal axis of the patient supporting table when the shockwave source 8 is already situated in the recess 9, such as in treatment cases that require the shockwave source 8 to be brought into engagement with the body 57 of the patient through the recess 9 (proceeding from the underside of the patient supporting table), the recess 9 has a clearance a (refer to FIG. 3) in the direction of the longitudinal axis of the patient support table that is greater than required by the corresponding dimension of the shockwave source 8, for example the diameter thereof. Although the clearance a is adequate when the support plate 1 is displaceable by approximately ±100 mm in the direction of the longitudinal axis of the patient supporting table when the shockwave source 8 is situated in the recess 9, the support plate 1 by itself cannot offer adequate support of the patient in the region of the recess 9 that has a clearance a of about 450 mm when the diameter of the shockwave source is approximately 250 mm.

In order to guarantee adequate support of the patient in the region of the recess 9 and, in particular, in order to prevent the patient from sliding through the recess 9, the base member 3 comprises a plate-shaped section 13, essentially adapted to the shape of the support plate 1, that is arranged under the support plate 1 so that its upper side 11 faces toward the underside 12 of the support plate 1. Similar to the support plate 1, the base member 3 also comprises a cut-out. Also similar to the support plate 1, the cut-out in the base member 3 is a recess 14 in what is the front longitudinal edge of the plate-shaped section 13 (illustrated in FIG. 1). A clearance b of the recess 14 in the direction of the longitudinal axis of the patient supporting table is provided so that the recess 14 is only slightly larger than the diameter of the shockwave source 8 and thus clearly is smaller than the clearance a of the recess 9 of the support plate 1.

It should be understood that, given a shockwave source 8 in engagement with the body 57 of the patient and that extends from the underside of the patient supporting table, the support plate 1 and the base member 3 must be arranged relative to one another such that the recess 9 of the support plate 1 leaves the recess 14 of the plate-shaped section 13 completely free, as shown in FIGS. 1 through 3 and 5. Since the support plate 1, as may be seen in FIGS. 1 through 3, has limiting edges 15 and 16 of its recess 9 that extend transversely relative to the longitudinal axis of the patient supporting table and, thus, transversely relative to the displacement direction lying essentially gap-free against the upper side 11 of the plate-shaped section 13, the upper side 11 of the plate-shaped section 13 offers an effective, additional support of the body 57 of the patient, this making it impossible for the patient to slide through the recess 9 of the support plate 1. That member of the upper side 11 of the plate-shaped section 13 of the base member 3 situated within the recess 9 of the support plate 1 thus forms an additional seating surface for the body 57 of the patient.

As can be seen in the Figures, the bearing surface of the support plate 1 is provided with a cushion 17 that extends up to the limiting edges 15 and 16 of the recess 9. It can be seen in FIG. 3 that it is thus assured that a distance of the body surface of the patient from the upper side 1 of the plate-shaped section 13 of the base member 3 in the immediate region of the limiting edges 15 and 16 of the recess 9 of the support 1 is provided. As a result, pinching of folds of skin between the support plate 1 and the plate-shaped section 13 is avoided during displacement of the support plate 1 relative to the base member 3.

In FIGS. 1 and 3, it is illustrated that the plate-shaped section of the base member 3 comprises two plate members 13a and 13b that, when viewed in the direction of the longitudinal axis of the patient supporting table and, thus, in the displacement direction, are arranged at different sides of the recess 14 of the base member 3. The plate members 13a and 13b have edges 52 and 53 that face toward one another and that define the limits of the recess 14.

The plate members 13a and 13b are connected to one another by a carrying beam 18. The carrying beam 18 extends under the longitudinal axis of the region 10 of the support plate 1 unaffected by the recess 9, i.e. along the back longitudinal edge of the support plate 1. The plate member 13b is connected to the base member 3. The carrying beam 18 and the plate member 13a attached to the carrying beam 18 thus form an effective support of the support plate 1 weakened by the recess 9, forming this effective support in the region of its free end. The plate member 13a acts as a bracket attached to the free end of the carrying beam 18 and by extending transversely relative to the longitudinal axis of the support plate 1 opposes twisting of the support plate 1.

Figure 4:
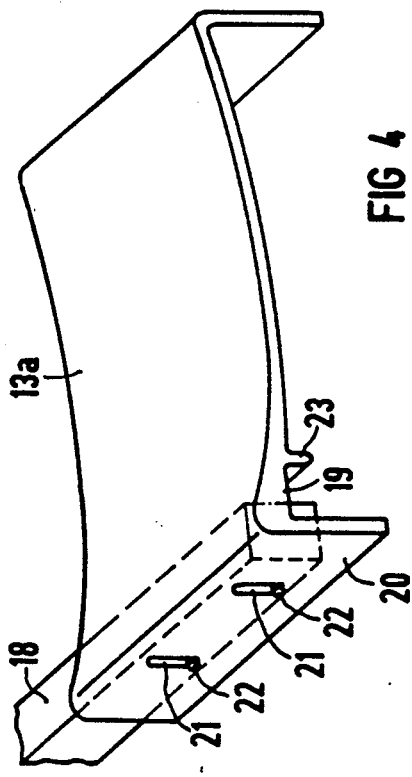
FIG. 4 is a perspective view of detail A of FIG. 1.

It should be clear, with reference to FIG. 4, that the plate member 13a has an approximately U-shaped section 19 at its end provided for fastening to the carrying beam 18. The section 19 embraces the carrying beam 18 from above, this carrying beam having an approximately rectangular cross-section.

The outer leg 20 of the U-shaped section 19 is provided with oblong holes 21 into which projections 22, applied to the outer lateral surface of the carrying beam 18, engage when the plate member 13a is attached to the carrying beam 18. The projections 22 thereby press against the lower limiting edges of the oblong holes 21. The plate member 13a can thus be separated from the carrying beam 18 in that it is lifted at its free end to such an extent that the inner leg 23 of its U-shaped section 19 is no longer in engagement with the inner lateral surface of the carrying beam 18 and in that it is then removed in an outward direction. The plate member 13a can also be reattached to the carrying beam 18 in a corresponding manner. It should be understood that the support plate 1 must be separated from the base member 3 for removing or, respectively, attaching the plate member 13a.

As shown particularly in FIG. 3, the carrying beam 18 is received in a corresponding guide bore 24 of the base member 3. A further carrying beam 26 is received in a further guide bore 25 (see FIGS. 2 and 5) situated at the other side of the base member 3.

The carrying beams 18 and 26 are guided and are longitudinally displaceable in their respective guide bores 24 and 25, so that it is possible to optionally extend one of the carrying beams 18 or 26 out of the base member 3 and to attach the plate member 13a to the extended carrying beam 18 or, respectively, 26. Proceeding from the situation illustrated in FIG. 1, wherein the recesses 9 and 14 are situated in the front longitudinal edge of the patient supporting table, there is the possibility of modifying the patient supporting table so that the recesses 9 and 14 are situated at the back longitudinal edge of the patient supporting table as illustrated in FIG. 5. All that is required for this purpose is to separate the support plate 1 from the base member 3, to separate the plate member 13a from the carrying beam 18, to insert the carrying beam 18 into the guide bore 24, to extend the carrying beam 26 out of its guide bore 25, to attach the plate member 13a to the carrying beam 26, and to reattach the turned patient supporting plate 1 to the base member 3.

In order to assure that the position of the recess 9 of the support plate 1 does not change with reference to the longitudinal axis of the patient supporting table when the support plate 1 is turned, the support plate 1 is constructed so as to be symmetric relative to an axis of symmetry S that extends transversely relative to the longitudinal axis of the patient supporting table and through the recess 9.

In order to guarantee the adjustability of the support plate 1 relative to the base member 3, the underside 12 of the support plate 1 that faces away from the seating surface 2 is constructed as a surface of action that presses against the upper side 11 of the plate-shaped section 13 of the base member 3 (that is also constructed as a surface of action). When the support plate 1 is displaced relative to the base member 3, the underside 12 of the support plate 1 and the upper side 11 of the plate-shaped section 13 of the base member 3 slide on one another. The support plate 1 and the plate-shaped section 13 of the base member 3 are largely matched to one another not only in view of their external dimensions, i.e. their length and width, but also in terms of their cross-section, so that not a punctual support but rather a large seating surface results between the underside 11 of the support plate 1 and the upper side 13 of the plate-shaped section 13 of the base member 3. The surface pressure between the two members 11 and 13 is thus only slight, so that significant wear does not occur. Similarly, for the sake of low wear, the upper side 11 of the plate-shaped section 13 of the base member 3 is formed by a friction-reducing coating 27, whereby the side of the coating 27 that faces toward the underside 12 of the support plate 1 then forms the actual plane of action of the base member 3. The friction-reducing coating 27 simultaneously provides that only a slight actuating force is required for the adjustment of the support plate 1. A polymeric material, namely polyethylene, can be provided as the material of the friction-reducing coating, as a result whereof the coating 27 is secured to the base member 3 in a simple manner, e.g., by gluing. In order to be able to secure the nut 56 to the support plate 1 in the required way, the plate-shaped section 13 is provided with a slot 61 that extends through the plate member 13b and the coating 27 and coincides with the slot 60 of the base member 3. The width of the slots 60 and 61 is limited to the dimension required for the passage of the nut 56.

As a consequence of the described construction of the underside 12 of the support plate 1 and of the upper side 11 of the plate-shaped section 13 of the base member 3 as surfaces of action, the support plate 1 constructed as a thin-walled, shell-shaped member receives uniform support, so that twistings and sags of the support plate 1 need not be feared.

The support plate 1 preferably is made of fiber-reinforced plastic, preferably carbon-fiber-reinforced plastic. As a result, it is then possible in a simple way to directly construct the underside 12 of the support plate 1 as a surface of action in a non-cutting manner during the manufacture of the support plate 1.

The plate-shaped section 13 of the base member 3 preferably is also formed of fiber-reinforced plastic, preferably carbon-fiber-reinforced plastic, so that here, too, the surface of the plate-shaped section 13 receives the required shape on the basis of non-cutting shaping during the manufacture thereof, this shape being required in order to obtain an upper side 11, after the coating 27 is glued on, that is suitable for interacting as described with the underside 12 of the support plate 1.

The adjustability of the support plate 1 in longitudinal direction of the patient supporting table is not restricted to the described ±100 mm. In order, for example, to be able to undertake endoscopic examinations, an adjustability of a total of approximately 700 mm can be established along the longitudinal direction of the patient supporting table. For this reason, the entire underside 12 of the support plate 1 preferably is constructed as a surface of action.

In the illustrated exemplary embodiment, the size of the surface of action, i.e. of the upper side 11 of the plate-shaped section 13 of the base member 3 amounts to approximately 60% of the area of the surface of action of the support plate 1. Since the entire upper side 11 of the plate-shaped section 13 of the base member 3 lies against the underside 12 of the support plate 1 in both extreme positions that the support plate 1 can assume with reference to the base member 3, a good support of the support plate 1 is always guaranteed. For that case wherein the entire underside 12 of the support plate 1 is not constructed as a surface of action, the surface of action of the base member 3 should cover at least 30% of the area of the underside 12 of the support plate 1. Moreover, it should be assured that at least 50% of the underside 12 of the support plate 1 always lies against the surface of action of the base member 3. The surfaces of action of both the support plate 1 as well as of the base member 3 need not necessarily be constructed as continuous surfaces but can be divided into a plurality of sections, as is the case, for example, when the upper side 11 of the plate-shaped section 13 of the base member 3, as a consequence of the fact that the plate-shaped section 13, comprising the two plate members 13a and 13b.

The surfaces of action of both the support plate 1 as well as of the plate-shaped section 13 of the base member 3 preferably extend up to the limiting edges 15 and 16 of the recess 9, or, respectively, the limiting edges 52 and 53 of the recess 14. The afore-mentioned, essentially gap-free seating of the limiting edges 15 and 16 of the recess 9 against the upper side 11 of the plate section of the base member 3 is thereby guaranteed.

In order to guarantee reliable guidance of the support plate 1 on the base member 3 transversely relative to the longitudinal axis of the patient supporting table, the support plate 1 preferably includes at both its longitudinal edges, guide rims 28 and 29 that are angled in a downward direction, these guide rims 28 and 29 having insides pressed against the corresponding longitudinal edges 58a and 59a or, respectively, 58b and 59b of the plate members 13a and 13b of the plate-shaped section 13 of the base member 3 (that are similarly angled in a downward direction). The insides of the guide rims 28 and 29 thereby represent component members of the surface of action of the support plate 1 and the outsides of the longitudinal edges 58a, 59a, 58b and 59b of the plate members 13a and 13b that are angled downwardly represent component members of the surface of action of the base member 3. The coating 27 therefore also covers the outsides of the longitudinal edges 58a, 59a, 58b and 59b.

The guide rim 28 applied to the longitudinal edge of the support plate 1 provided with the recess 9 is, of course, discontinuous in the region of the recess. The guide rims 28 and 29 have the insides of their free ends provided with ledges 30 and 31 that, proceeding from below, press against the angled-off longitudinal edges of the plate members 13a and 13b of the plate-shaped section 13 of the base member 3, whereby the ledge 30 is interrupted in the region of the recess 9 of the support plate 1. A reliable cohesion of the support plate 1 to the base member 3 is thus guaranteed, particularly when pivoting the patient supporting table in the direction of the curved double arrow x and/or of the curved doubled arrow y.

In order to be able to turn the patient support plate 1. This support plate must be separated from the drive means 54, 55, and 56 serving the purpose of displacing the support plate 1 in the directions of the double arrow x and must be withdrawn from the base member 3 in the direction of the longitudinal axis of the patient supporting table. The support plate 1 is then turned and subsequently slipped back onto the base member 3 in its rotated position and coupled to the drive means. For separating the drive means 54, 55, and 56 from the support plate 1, the nut 56 is detached from the support plate 1 by unscrewing a screw (not shown) that is accessible from the upper side of the support plate 1, this screw serving to fasten the nut 56 to the support plate 1.

The support plate 1 preferably is provided with rails 32 and 33 having a circular cross-section that extends along its longitudinal edges. The rail 32 attached to the longitudinal edge of the support 1 provided with the recess 9 is, of course, discontinuous in the region of the recess 9.

The rails 32 and 33 serve to permit fastening of accessory members to the support plate 1, as indicated in FIG. 1 with reference to the example of an infusion stand 34 and of a foot rest 35. The infusion stand 34 and the foot rest 35 are provided with suitable clamp devices that allow these members to be fastened at a desired position along the support plate 1.

As may be seen from FIG. 1, there is the possibility of closing the recess 9 of the support plate 1 with a closure member 36 that is supported by the plate members 13a and 13b of the plate-shaped section 13 of the base member 3. To this end, the closure piece 36 can be placed into the recess 9. Preferably, the closure piece 36 is provided with a cushion 37 whose thickness corresponds to that of the cushion 17.

Figure 6:
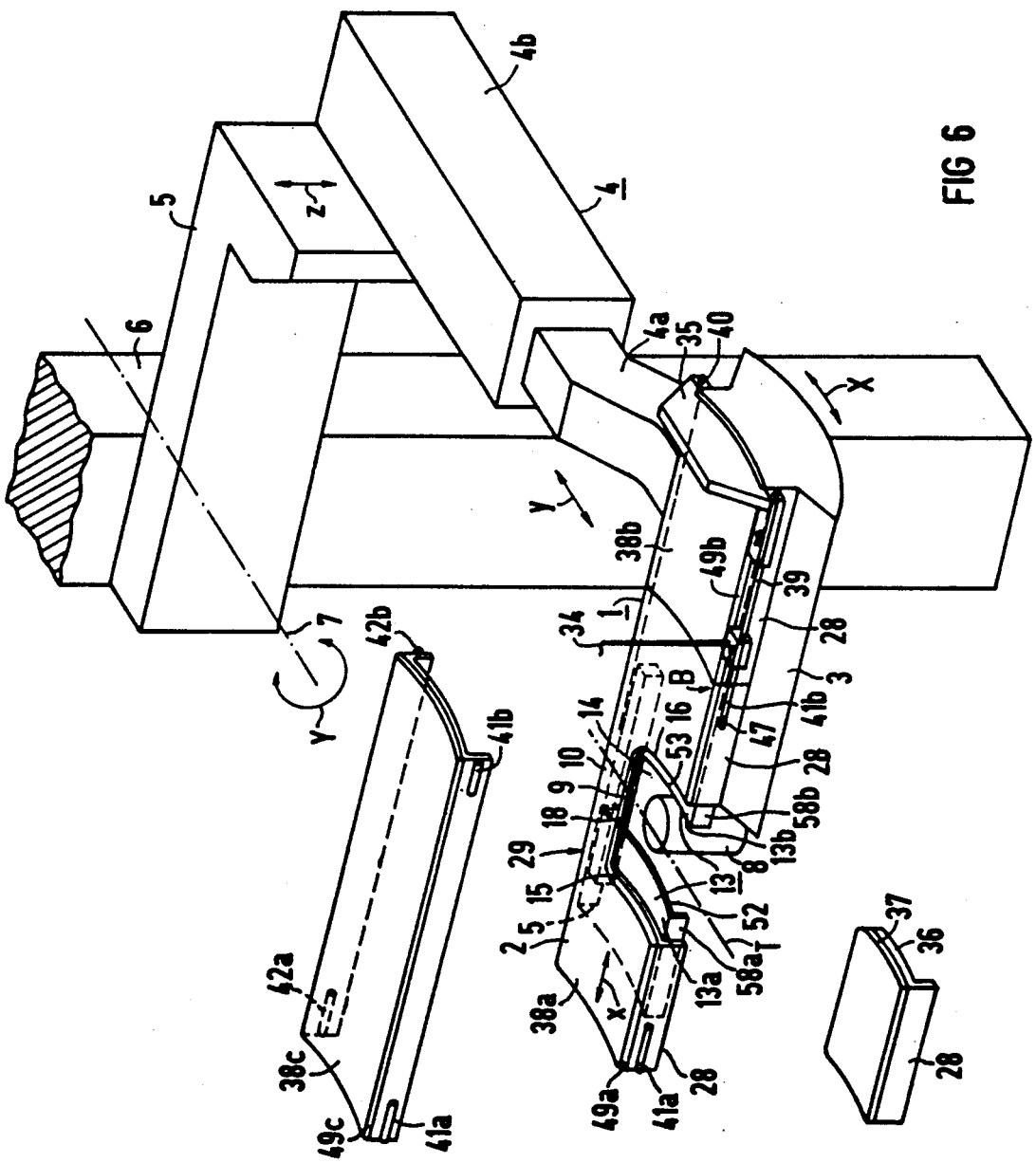
FIG. 6 is a perspective view of another patient supporting table.
Figure 7:
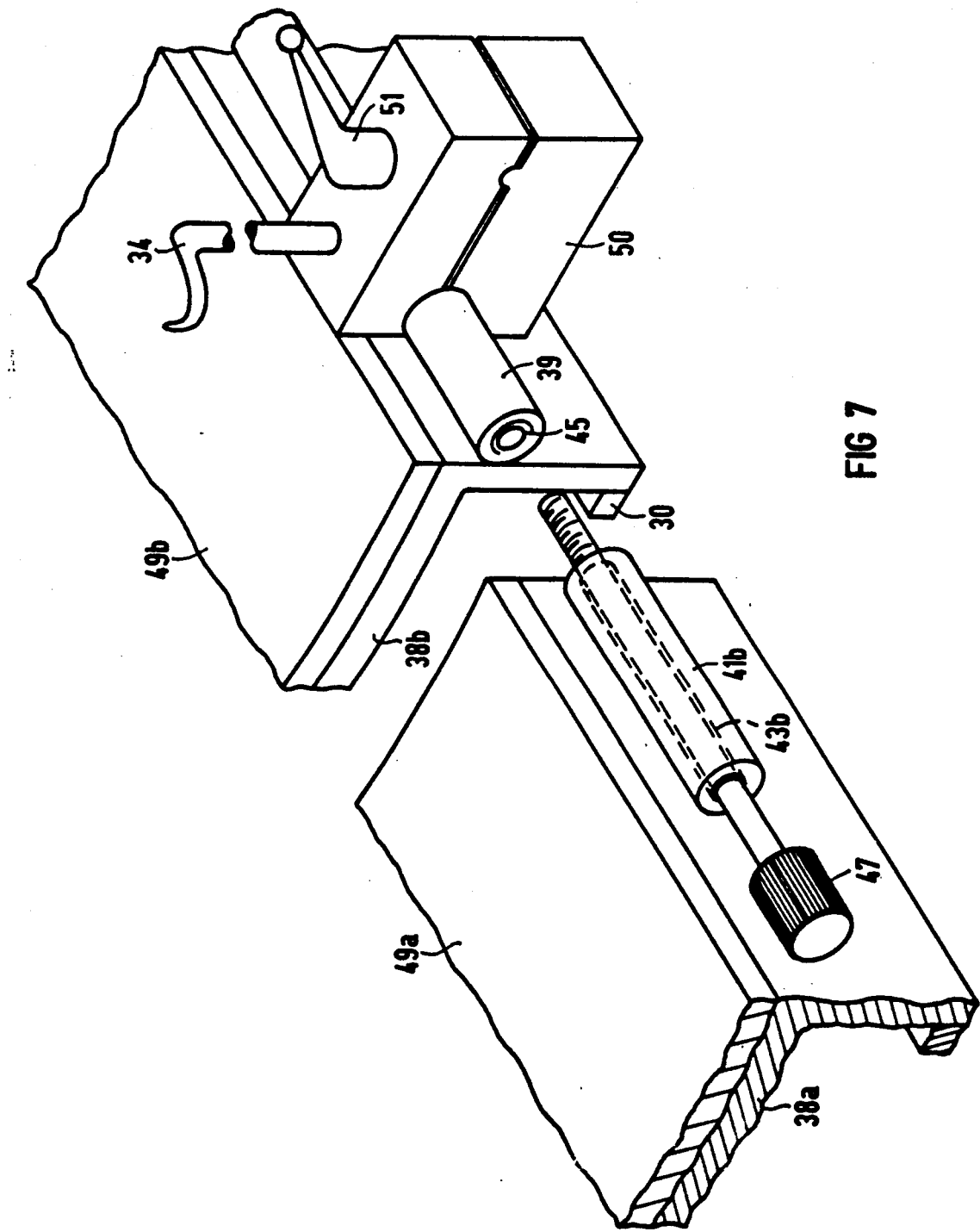
FIG. 7 is an exploded perspective view of detail B of FIG. 6.

In FIGS. 6 and 7 there is illustrated a second exemplary embodiment of a patient supporting table of the invention that differs from the above-described exemplary embodiment with respect to the construction of the support plate 1. Accordingly, the reference numerals and characters used in the preceding figures are also used to identify identical parts in FIGS. 6 and 7.

As illustrated in FIG. 6, the support plate 1 is constructed to be bipartite and comprises plate sections 38a and 38b which are joined to one another. The plate section 38a forms the free end of the patient supporting table and is provided with the recess 9. The drive means (not shown) that serves to displace the support plate 1 along the directions of the double arrow x has its nut engaging the plate section 38b, which is attached to the base member 3.

As further illustrated, the plate section 38b is provided with rails 39 and 40 that extend along its longitudinal edges and have a circular cross-section. The rails 39 and 40 serve to permit fastening accessory members, for example the infusion stand 34 and the foot rest 35.

Rail sections of which only rail sections 41a and 41b are visible in FIG. 6, are provided at the longitudinal edges 28 and 29 of the plate section 38a. As illustrated in FIG. 7, the rail sections are provided with axial through bores. This can be seen with reference to rail section 41b which is provided with a bore 43b. It can be seen in FIG. 7, with reference to the rail 39 and its associated threaded bore 45, as an example, those ends of the rails 39 and 40 facing away from the base member 3 are provided with threaded bores that align with the bores of the rail sections when the plate section 38a is placed in proper position on the plate-shaped section 13 of the base member 3. As also can be seen from FIG. 7, with reference to the rail section 41b with the bore 43b, as an example, the rail 39 with associated threaded bore 45 and the knurled screw 47, the two plate sections 38a and 38b of the support plate 1 are detachably joined to one another with the assistance of knurled screws that can extend through the bores of the rail sections and can be screwed into the threaded bores of the rails 39 and 40.

When the knurled screws are removed, the plate section 38a can be axially withdrawn from the plate-shaped section 13 of the base member 3 turned around and placed back onto the plate-shaped section 13 of the base member 3, so that the recess 9 situated in the plate section 38a of the support plate 1 can be selectively positioned in the back or in the front longitudinal edge of the support plate 1. It should be understood that only the carrying beam 18 or, respectively, the carrying beam 26 is withdrawn from the base member 3 and is provided with the plate member 13a.

In contrast to the exemplary embodiment set forth previously, the separation of the drive means from the support plate 1 is superfluous when turning the plate section 38a because of the division of the support plate 1 into the two plate sections 38a and 38b. In order to assure that the position of the recess 9 with respect to the longitudinal axis of the patient supporting table does not change when the plate section 38a is turned, the plate section 38a, as in the case of the above-described exemplary embodiment of the support plate 1, is made to be symmetric relative to an axis of symmetry T that extends through the recess 9 transversely relative to the longitudinal axis of the patient support table.

However, similar to the above-described exemplary embodiment, there is the possibility of closing the recess 9 of the plate section 38a with the closure piece 36 provided with the cushion 37. Both plate sections 38a and 38b, can also be provided with cushions such as cushion 49a and 49b, respectively.

As illustrated in FIG. 6, there is also the possibility, in treatments that would allow this, of joining a plate section 38c constructed without a recess to the plate section 38b instead of joining the plate section 38a thereto. In this case, the plate section 38c preferably is provided with a cushion 49c. The plate section 38c is illustrated with all four rail sections 41a, 41b, 42a, and 42b showing.

It may be seen in FIG. 7 that the infusion stand 34 is provided with a clamp-like clamp member 50 that can be clamped on the rail 39 with a locking screw 51. The fastening of the foot rest 35 is fastened to the rail 39 in a similar manner (not shown). In the case of the exemplary embodiment of FIGS. 1-5, the infusion stand 34 and of the foot rest 35 are fastened to the rails 32 and 33 in the same manner.

It can be appreciated that the exemplary embodiments are directed only to patient supporting tables that are a component member of a work station for treating a patient with focused shockwaves for non-invasive disintegration of calculi situated in the body of the patient. However, x-ray examination tables, patient supporting tables for urology, supporting tables for radiation therapy, etc., can also be constructed so as to embody the invention. Moreover, in the case of the exemplary embodiments, only adjustment of the support plate 1 relative to the base member 3 in the direction of the longitudinal axis of the patient supporting table and on a straight line is provided. However, other and/or additional adjustment possibilities, can be realized with the features of the invention.

While a preferred embodiment has been shown, modifications and changes may become apparent to those skilled in the art which shall fall within the spirit and scope of the invention. It is intended that such modifications and changes be covered by the attached claims.

I claim:

1. A patient supporting table comprising:
   a support plate with a seating surface for a patient and a cut-out through which the body surface of a patient lying on the seating surface is accessible; and
   a base member that carries the support plate, the support plate being adjustable relative to the base member, the base member being positioned beneath the support plate and comprising an upper side that faces toward an underside of the support plate, the base member including an opening extending through the upper side thereof whose extent in an adjustment direction is less than a corresponding extent of the cut-out of the support plate, the support plate being positionable relative to the base member such that the cut-out of the support plate exposes the opening of the base member over the entire extent of the opening in the adjustment direction and the upper side of the base member forming an additional seating surface within the cut-out of the support plate.

2. The patient supporting table of claim 1, wherein limiting edges of the cut-out of the support plate that extend transversely relative to the adjustment direction abut essentially gap-free against the upper side of the base member.

3. The patient supporting table of claim 1, wherein the seating surface of the support plate is provided with a cushion that extends up to edges of the cut-out of the support plate.

4. The patient supporting table of claim 1, wherein the support plate is constructed as a thin-walled component member.

5. The patient supporting table of claim I, wherein the underside of the support plate comprises a surface of action, said surface of action pressing-flatly against a correspondingly shaped surface of action of the base member, the surfaces of action extending to edges of the supporting plate cut-out and of the base member opening that extend transversely relative to the adjustment direction, and the surfaces of action sliding on one another given adjustment of the support plate relative to the base member.

6. The patient supporting table of claim 1, wherein the supporting plate cut-out is a recess in a limiting edge of the support plate and the base member opening is a recess in a corresponding limiting edge of the base member.

7. The patient supporting table of claim 6, wherein the base member comprises two plate members that are positioned at different sides of the opening of the base member, the plate members being joined to one another by a carrying beam that extends along an edge of the support plate lying opposite the cut-out of the support plate, the carrying beam extending at least in the region of the cut-out of the support member.

8. The patient supporting table of claim 6, wherein the support plate can be attached to the base member such that the support plate recess is positioned at either side of the patient supporting table.

9. The patient supporting table of claim 1, wherein the support plate comprises two releasably securable plate members, one plate member including the support plate cut-out.

10. The patient supporting table of claim 8, comprising two carrying beams that are optionally extendable, depending on the position of the cut-out of the support plate, at either side of the patient supporting table.

* * * * *